(12) United States Patent
Krans et al.

(10) Patent No.: US 10,004,454 B2
(45) Date of Patent: Jun. 26, 2018

(54) BREATH PACING DEVICE AND METHOD FOR PACKING THE RESPIRATORY ACTIVITY OF A SUBJECT

(75) Inventors: Jan Krans, Den Bosch (NL); Bartel Van De Sluis, Eindhoven (NL); Juergen Vogt, Eindhoven (NL); Ronaldus Aarts, Geldrop (NL); Tim Tijs, Helmond (NL); Bernardo Arnoldus Mulder, Dronrijp (NL); Paulus Dillen, Eindhoven (NL); Georgo Zorz Angelis, Oss (NL); Roy Raymann, Waalre (NL); Petronella Zwartkruis-Pelgrim, Nuenen (NL); Jia Du, Eindhoven (NL); Ype Brada, Leeuwarden (NL); Maarten Van Den Boogaard, Westerbroek (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 215 days.

(21) Appl. No.: 13/885,167

(22) PCT Filed: Nov. 16, 2011

(86) PCT No.: PCT/IB2011/055118
§ 371 (c)(1),
(2), (4) Date: Aug. 8, 2013

(87) PCT Pub. No.: WO2012/069962
PCT Pub. Date: May 31, 2012

(65) Prior Publication Data
US 2013/0310636 A1 Nov. 21, 2013

(30) Foreign Application Priority Data
Nov. 23, 2010 (EP) ..................................... 10192276

(51) Int. Cl.
*A61B 5/08* (2006.01)
*A61B 5/00* (2006.01)

(52) U.S. Cl.
CPC ................. *A61B 5/486* (2013.01); *A61B 5/08* (2013.01)

(58) Field of Classification Search
CPC ......... A61B 5/08; A61B 5/087; A61B 5/0878; A61B 5/486
See application file for complete search history.

(56) References Cited

U.S. PATENT DOCUMENTS

| 4,064,869 A | 12/1977 | Defares et al. |
| 5,853,005 A | 12/1998 | Scanlon |

(Continued)

FOREIGN PATENT DOCUMENTS

| EP | 2311533 A1 | 4/2011 |
| GB | 1343793 | 1/1974 |

(Continued)

OTHER PUBLICATIONS

Motoyuki Akamatsu et al, "Mouse Type Interface Device With Tactile and Force Display—Multi-Modal Integrative Mouse -", Industrial Products Research Institute, Tsukuba, Japan pp. 177-182.

(Continued)

*Primary Examiner* — Thaddeus Cox

(57) ABSTRACT

The present invention is related to a breath pacing device (10) for pacing the respiratory activity of a subject, comprising an output unit (12) for outputting a sequence of output signals, a control unit (16) provided to control the output unit, and an input unit (14) connected to or integrated into the output unit for generating an input signal related to a respiration characteristic of a subject. The control unit is provided to control the length of the sequence at least based on characteristics of the input signal. The invention is further (Continued)

related to a corresponding method for pacing the respiratory activity of a subject.

16 Claims, 6 Drawing Sheets

(56) References Cited

U.S. PATENT DOCUMENTS

| | | | |
|---|---|---|---|
| 7,691,049 B2 | 4/2010 | Wood et al. | |
| 2004/0116784 A1* | 6/2004 | Gavish | 600/300 |
| 2006/0047202 A1 | 3/2006 | Elliott | |
| 2006/0102171 A1 | 5/2006 | Gavish | |
| 2006/0258916 A1 | 11/2006 | Pietersen | |
| 2007/0114206 A1 | 5/2007 | Mitrovic | |
| 2007/0203433 A1 | 8/2007 | Murphy | |
| 2008/0108903 A1* | 5/2008 | Ben-Oved et al. | 600/484 |
| 2009/0114216 A1 | 5/2009 | Hung | |
| 2009/0192402 A1* | 7/2009 | Corn | 600/534 |
| 2010/0112537 A1 | 5/2010 | Dobson | |
| 2011/0034820 A1 | 2/2011 | Pietersen | |
| 2011/0046518 A1* | 2/2011 | Fischer | 600/594 |

FOREIGN PATENT DOCUMENTS

| | | | | |
|---|---|---|---|---|
| JP | | 04348760 A | 12/1992 | |
| JP | | 2005011491 A1 | 2/2005 | |
| JP | | 2005040440 A | 2/2005 | |
| JP | | 2005137896 A | 6/2005 | |
| JP | | 2005152462 A | 6/2005 | |
| JP | | 2005535378 A | 11/2005 | |
| JP | | 2006055625 A | 3/2006 | |
| JP | | 2006136515 A | 6/2006 | |
| JP | | 2007501664 A | 2/2007 | |
| JP | | 2007512086 A | 5/2007 | |
| JP | | 2007260015 A | 10/2007 | |
| JP | | 2010213773 A | 9/2010 | |
| WO | | 2005055802 A2 | 6/2005 | |
| WO | | 2007079068 A2 | 7/2007 | |
| WO | WO 2008110956 A1 * | | 9/2008 | ........... A61B 5/0205 |
| WO | | 2008139380 A2 | 11/2008 | |
| WO | WO 2008139380 A2 * | | 11/2008 | ........... A61B 5/0816 |
| WO | WO 2011045709 A1 * | | 4/2011 | ......... A61B 5/02416 |

OTHER PUBLICATIONS

"Breathe with the Ocean" Dijk et al, Philips Research, High Tech. Campus, 34 Eindhoven, NL Created Aug. 24, 2010, 12:08:43PM.
"EuroHaptics 2010" Proceedings of the EuroHaptics 2010 Special Symposium, Amsterdam, Jul. 7, 2010, Anton Nijholt et l (eds.).
"Squeeze Me: A Portable Biofeedback Device for Children" Amy Parness et al, New York University, Interactive Telecommunications Program, (undated).
Ferriss, "Sleep Better. Work Better. Live Better", Fall Asleep Naturally With Nightwave, Downloaded From http://www.nightwave.com/index.php, Feb. 22, 2016.
Hauri, "Evaluation of a Sleep Switch Device", Sleep, vol. 22, No. 8, 1999, p. 1110-1117.
Li et al, "Comparison of Respiratory-Induced Variation S in Photoplethysmographic Signals", Physiological Measurement, vol. 31, No. 3, 2010, p. 415-425.
Modern Device Wind Sensor Rev.C, Downloaded From https://moderndevice.com/product/wind-sensor/ on Jan. 18, 2017, 3 Pages.

* cited by examiner

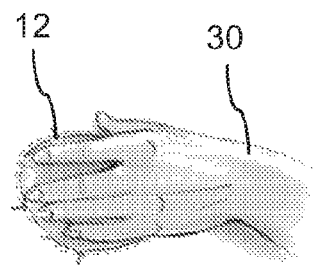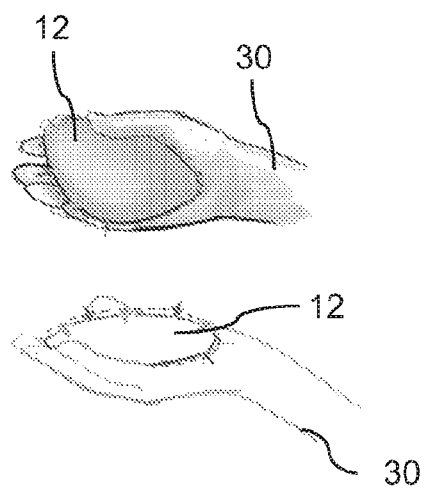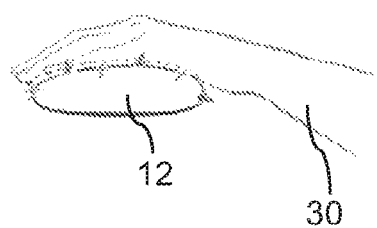
Fig. 5        Fig. 6
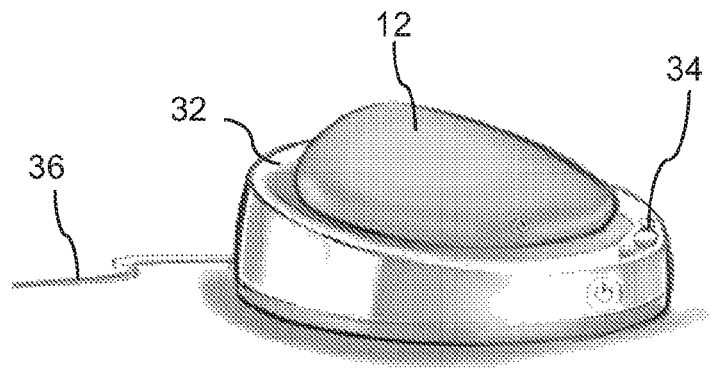
Fig. 7

BREATH PACING DEVICE AND METHOD FOR PACKING THE RESPIRATORY ACTIVITY OF A SUBJECT

FIELD OF THE INVENTION

The invention relates to the field of pacing the respiratory activity of a subject, especially to a breath pacing device and a corresponding method for pacing the respiratory activity of a subject.

BACKGROUND OF THE INVENTION

A slow and regular breathing activity is considered to be beneficial for relaxation. To support the breathing process, several different breath pacing devices are known to provide output signals that correspond to a desired regular breathing rhythm and can easily be perceived by a user.

US20070114206 discloses a breath pacing device comprising respiration sensors for producing a breath condition signal that is displayed to a user as a feedback. On the reception of this signal, the user can adapt his respiration practice for learning purposes. In this case the sensors are integrated into an article of clothing like a shirt, for example, so that this device is not suitable for each situation in which a relaxation is desired.

A pacing signal can also or alternatively be, for example, a light that changes its intensity, color or shape periodically according to the desired respiration cycles. In one possible application, breath pacers can be used in bed by a person to reduce sleep onset latency. These breath pacers project a light spot of slowly varying size on the ceiling of the bedroom. A further example for a pacing signal could be an audio or video signal.

SUMMARY OF THE INVENTION

For an application as described above, it is desired to design a breath pacing device as consumer product that can be conveniently used in a home situation like, for example, in a bedroom. Experience has shown that such products are only accepted by the user when their design allows an easy and convenient control of all its functions. The interaction between the device and the subject should be as easy and intuitive as possible. For this reason a relatively simple construction of the pacing device is essential, including a suitable arrangement of the input unit for generating the input signal related to the respiration characteristic of the subject. Moreover, a further problem related to the user-friendliness of pacing devices is that their operation is found to be disturbing when they continue to run for a longer time period than necessary. For example, the breath pacing device to be used in bed to assist a person to fall asleep may disturb this person when it operates through the night until the morning. On the other hand, it should not stop to operate until a sufficiently relaxed or sleeping state is achieved.

It is therefore an object of the present invention to provide a breath pacing device that offers an improved design and user friendliness compared to the breath pacing devices known from the state of the art. Another object is to provide a corresponding method for pacing the respiratory activity of a subject.

This object is achieved by a breath pacing device as well as by a corresponding method as claimed in the independent claims. The dependent claims define advantageous embodiments.

According to an embodiment of the present invention, the breath pacing device comprises an input unit for generating the input signal. The input unit may be connected to or integrated into the output unit. Also the control unit may be integrated in the output unit. Thus, in a preferred embodiment the input unit is connected to the control unit and both are integrated in the output unit. This arrangement allows a compact design that is found to be used by a user in a convenient way. For example, the input unit can be directly integrated into the surface of a tactile output unit so that it is not perceived as an additional operation unit of the device. This highly improves the acceptance of the pacing device by the consumer. However, there are other possibilities to connect the input unit to the output unit conveniently. The input unit could be directly attached to the tactile output unit; it could be connected to it by a suitable connecting means. Several alternatives could be conceived in this respect.

Moreover, the control unit is provided to control the length of the sequence of output signals perceivable by the subject, i.e. the period of the pacing operation in a convenient way. This means that the breath pacing device is controlled at least based on characteristics of the input signal. This allows an input signal-responsive output for an adaptive breathing exercise, or an automatic turn off of the output unit on the basis of the present respiration activity of the subject or on a time schedule that may be calculated by the control unit or be based on a user input. The time schedule can be chosen such that it provides a sufficient operating time to reach the relaxation effect but avoids running the pacing device much longer than necessary. If the control is based on characteristics of the input signal, it is possible to turn the pacing device off or to set it into a standby mode when it has been determined that the subject has reached the desired relaxed or sleeping status.

According to a preferred embodiment of the present invention, the output unit is provided as a tactile output unit for outputting tactile output signals. This embodiment provides the advantage that the generated output signals are haptically perceivable, which also contributes to the user friendliness of the breath pacing device. It works in a dark environment and can be used without disturbing other persons. Examples for tactile output units are cushions, pillows, pads, stuffed toys, mobile phones, wristbands, watches or the like. However, these embodiments are not understood as limiting but the tactile output unit can have any other suitable size or shape.

According to one preferred embodiment of the present invention, the input unit is arranged at the surface of the output unit or integrated inside the output unit. An arrangement of the input unit at the surface provides the advantage that it allows a compact design of the input unit inside the output unit but still makes it accessible from the outside. A full integration into the output unit may also be possible in many cases. For example, a completely integrated input unit may register movements of the output unit and to interpret them as an input signal.

According to a preferred embodiment, the input unit is represented by a sensor for sensing a characteristic of the subject and/or by a user interface receiving a user input for adjusting a characteristic of the sequence of tactile output signals. The sensor can be used, for example, to monitor the respiration activity of the subject and to generate a corresponding input signal, indicating certain respiratory characteristics. On this basis the control unit can control the length of the sequence of output signals. A user interface provides the possibility to accept inputs from the user, for example, to choose a desired length of the sequence and the operation period of the breath pacing device.

According to other preferred embodiments, the sensor is at least one of a body motion sensor for detecting a body motion of the subject, such as a radar sensor, an accelerometer or a camera, a pressure sensor for detecting a mechanical pressure applied to the subject, a photopletysmographic (PPG) sensor, an airflow sensor, or a weight sensor.

According to one further preferred embodiment, the pressure sensor comprises a pressure sensitive foil.

In case an airflow sensor is used to detect air flow during exhalation (for instance when blowing) and/or inhalation, this airflow sensor may comprise a temperature sensing element. Such an element can be, for example, a thermistor whose resistance varies with temperature. Temperature differences in inhaled and exhaled air can be interpreted to determine the inhale and exhale phases of the respiratory activity. A microphone can also be used as an airflow sensor.

In the case wherein the input unit is represented by a user interface, this user interface is preferably represented by at least one of a mouse wheel, a keyboard, at least one button, a touch screen, a touch pad, a squeeze sensor, a pressure switch or a microphone. The microphone could be provided, for example, with voice recognition capability. The squeeze sensor or pressure switch can be triggered by the user at the start of inhalation and/or exhalation to align with the user's own respiration and/or inhalation and exhalation times.

Preferably the user interface is adapted to receive a user input to determine a characteristic of a subject, to receive a user input to start or stop the outputting of a sequence of output signals and/or to output status information of the breath pacing device. Such status information can be, for example, the length of the chosen time schedule or the like that can be displayed with help of a screen or any other suitable output device.

According to one embodiment of the present invention, the user interface is adapted to receive a user input to stop the outputting of a sequence of tactile output signals.

According to another preferred embodiment the input unit is adapted to determine a characteristic of a subject and to receive a user input.

According to another preferred embodiment, the input unit is provided to generate an input signal related to at least one of the respiration frequency, the respiration amplitude, an age or identification of the subject, the time of day, or the day of week. These are examples for certain characteristics from which a suitable length of the sequence of the output signals can be derived.

According to another embodiment, the control unit is provided to control the output of a sequence of tactile output signals at least based on an input signal received from the sensor and/or received from the user interface, wherein the control is further based on previously stored characteristics and/or a previously stored algorithm. This includes the possibility to acknowledge sensor signals as well as active inputs by the subject via the user interface and to control the length or characteristic of the sequence of output signals accordingly.

According to another preferred embodiment, the control unit is provided to generate a stopping signal upon the generation of an input signal related to a sleeping or relaxed state of the subject and/or after a predetermined time period has lapsed. Upon the generation of the stopping signal the tactile output unit stops the output of the sequence of tactile output signals.

According to another preferred embodiment, the output unit is represented by a least one of a cushion, a pillow, a pad, a stuffed toy, a wristband, a mobile phone, or a watch.

Preferably, the breath pacing device according to the present invention comprises a rechargeable power supply. This enables a wireless operation of the pacing device without any disturbing connections to a mains supply, further improving its user friendliness.

The invention is further related to a method for pacing the respiratory activity of the subject, comprising: receiving an input signal from an input unit related to a respiration characteristic of a subject; controlling an output unit to output a sequence of output signals according to the received input signal; and stopping the sequence of output signals at least based on the recognition of predetermined characteristics of the input signal.

The breath pacing device may preferably include a temperature controlling element, which could be used to warm up the pacing device. Such temperature controlling element could be realized as a heating element, which is just controlled to have fixed temperature and/or which may have a temperature sensor for sensing the temperature of the user who contacts the pacing device. By warming up the device convenience of the user in increased. Thus in case of a cushion or hand pad or the like people having colder hands or feeling cold may feel more comfortable. On the other hand it can increase feeling of connectedness with the breathing device. This temperature control of the pad can be realized by integration of a heating element in the pad.

These and other aspects of the invention will be apparent from and elucidated with reference to the embodiments described hereinafter.

BRIEF DESCRIPTION OF THE DRAWINGS

These and other aspects of the invention will be apparent from and elucidated with reference to the embodiments described hereinafter. In the drawings:

FIGS. 5 and 6 are further embodiments of a breath pacing device according to the present invention in use by a subject;

FIG. 7 shows an embodiment of the breath pacing device of FIG. 5 or 6 together with a docking station;

DETAILED DESCRIPTION OF EMBODIMENTS

Figure 1:
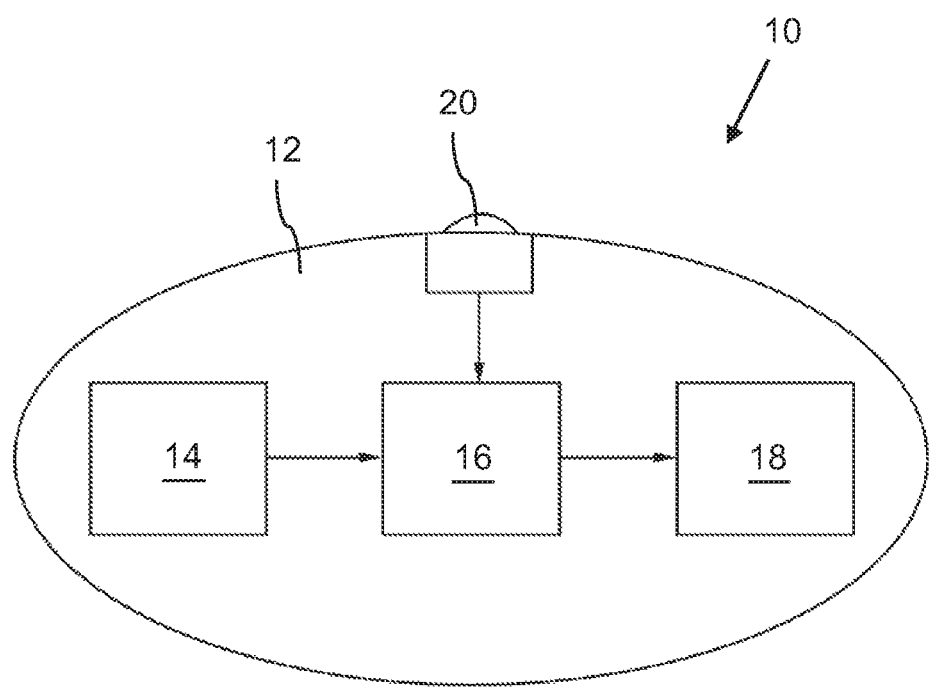
FIG. 1 is a schematic cross section through one embodiment of a breath pacing device according to the present invention.

The breath pacing device in FIG. 1 is provided as a tactile breath pacing device 10 comprising a tactile output unit 12 that determines the outer shape and appearance of the pacing device 10. As will be exemplary described, all functional components of the tactile breath pacing device 10 are integrated into this tactile output unit 12. A tactile breath pacing device 10 is only one example of a breath pacing device according to the present invention, and its tactile output unit 12 may be replaced by any other suitable output unit for generating output signals that can be perceived by a subject, for example, by an acoustic output unit and/or a visual output unit or a combination thereof. The following description will refer to a tactile breath pacing device 10 without limiting the scope of the present invention in this respect. It is alternatively possible to arrange the input unit and the control unit outside from the output unit and to provide the signals required for controlling the output unit wired or wireless to the output unit. Further, it is possible to adjust the starting characteristic at a docking station and to transfer the setting to the output unit, whereas the output unit itself may include at least a sensor or a switch off button to further control the sequence of output signals during use of the device.

In the present example, the tactile output unit 12 is a cushion or pad, although it can have different kinds of shapes and sizes. However, it could alternatively be realized as wristband. The cushion or pad is provided to change its size periodically, especially its thickness, and this change is a tactile output signal perceivable by a subject that is in close contact with the tactile output unit 12. The tactile output signals outputted by the tactile output unit 12 serve to pace the respiratory activity of the subject.

A sensor 14 as an input unit may be integrated into the tactile output unit 12 to determine a respiration characteristic, especially the respiration rate of the subject. In the present embodiment, the sensor 14 may be e.g. an airflow sensor represented by a microphone. Blowing against the microphone is interpreted as an exhale activity of the subject, while the time intervals between two blowing intervals are interpreted as inhale phases. To measure this airflow, the sensor is placed directly at the surface of the tactile output unit 12. Under technical aspects the airflow sensor does not necessarily have to be a microphone but can alternatively be represented by other types of sensors, for example, by an anemometer or a temperature sensing element like a thermistor. A thermistor is a type of resistor whose resistance varies with temperature. Temperature differences in inhaled and exhaled air can be interpreted to identify the inhale and exhale phases of the respiration activity. Moreover, one option is to use the sensor to analyze the chemical composition of the exhaled air and to measure the percentage of $CO_2$ contained therein. This information can further be used to determine the character of the breathing activity and to adapt the pacing characteristics thereto.

Alternatively, the airflow sensor used in this embodiment as the sensor 14 could be replaced by or used in addition to a body motion sensor to monitor the respiratory activity of the subject. This embodiment is based on the idea that the respiratory activity leads to periodic movements of the subject's body that can be easily measured by a body motion sensor. An accelerometer is one example for such a body motion sensor to determine the respiration rate from chest or belly movements. Compared to an airflow sensor, it provides the advantage that it can be completely integrated in the tactile output unit 12 without being accessible from the outside. When no movement is measured for a certain amount of time, this state can be interpreted as a situation where there is no contact of the subject with the tactile output unit 12, and the tactile breath pacing device 10 can automatically be turned off. This is also possible in the embodiment using the airflow sensor, interpreting a lack of input for a certain amount of time, i.e. no airflow to be measured by the blow sensor as a situation in which the tactile breath pacing device 10 is not used. Another possibility is that an accelerometer used as a sensor 14 detects a sudden drop of the device, indicating that the user has released the device to let it drop because she/he has fallen asleep, and this is taken as a signal to switch off.

The body motion sensor can also comprise a motion detector in form of a drop of current conducting material that can move between a position where it facilitates a current flowing between electrodes and a position where no current can flow, such that the current is modulated by the movement of the drop. As described above, such a mechanism can be used to shut down the tactile pacing device 10 or setting it into a standby mode when no modulation takes place.

Another embodiment of the sensor 14 is a photopletysmograph (PPG) to analyze a respiratory pattern from a blood volume pulse signal. In one common embodiment, the skin of the subject (for example, on a finger or wrist) is illuminated and the change of light absorption due to the respiratory activity as measured. The user can operate the photopletysmograph by placing her/his finger on top of a window present at the surface of the tactile output unit 12.

Alternatively and/or additionally an externally arranged radar sensor could be used for measuring a body's motion to derive the input signal related to the respiration signal. It is alternatively possible to use a camera as a sensor for this purpose. Another embodiment of such a remote body motion sensor is a weight sensor or a pressure sensor for detecting a mechanical pressure applied by the subject, corresponding to her/his respiration activity. Such a sensor may comprise a pressure sensitive foil.

Further operation units of the tactile breath pacing device 10 are a control unit 16 and an actuator 18, both being integrated into the tactile output unit 12. The control unit 16 receives an input signal from the sensor 14 indicative of a respiratory characteristic of the subject. The sensor 14 generates this respiration signal according to the measured respiration characteristic. The control unit 16 is provided to analyze the input signal and to search for signal patterns contained within the input signal. Moreover, the control unit 16 is provided to control the actuator 18 according to the result of this analysis, as will be described in the following. The actuator 18 is provided to induce a movement of the tactile output unit 12 to output the tactile output signals. That is, according to the movement of the actuator 18, the tactile output unit 12 moves, and this motion is perceivable by the subject. For example, the tactile output unit 12 can increase or decrease its size or can change its outer shape. However, other haptically or tactile perceivable changes of the outer appearance of the tactile output unit 12 can be taken into account. The tactile output unit 12 can also perform haptically perceivable clicks or other force actions to give a perceivable signal to the user.

The tactile breath pacing device 10 may further comprise a rechargeable power supply (not shown) like a rechargeable battery or an accumulator, so that the whole device may operate wirelessly.

The tactile output unit 12 is activated to output a sequence of tactile output signals when an input signal is generated. In the present embodiment, this starting signal is generated by the control unit 16 when a signal pattern has been recognized within the input signal being a respiration signal. This means that at least one respiration characteristic, for example, the respiration rate has been identified in the input signal. If this is the case, the control unit 16 controls the actuator 18 to initiate a sequence of tactile output signals that comprises a signal pattern that is related to the signal pattern that has been recognized. For example, these tactile output signals have the same or a similar frequency or amplitude as the measured respiration signals. Another possibility is that the signal pattern of the generated tactile output signals has a certain relation to the recognized signal pattern. Just to give one example, the frequency of the tactile output signals may be somewhat lower than the measured respiration rate. Also, the ratio between expand and contract time of the actuator maybe somewhat different than the inhale to exhale ratio measured by the respiration sensor. The control unit 16 may comprise a computer program to control the actuator 18 accordingly.

By generating a sequence of tactile output signals with a signal pattern that is related to the recognized signal pattern, it is possible to synchronize the generated tactile output signals to the present respiration behavior of the subject. In the present embodiment the tactile output unit 12 does not generate tactile output signals until a signal pattern has been recognized within the input signal by the control unit 16. Once a pattern has been recognized, the starting signal is generated for the tactile output unit 12 to begin with the output of the sequence of tactile output signals. It is alternatively possible to begin with the generation of tactile output signals earlier without being influenced by a measurement and to start the output of the sequence of tactile output signals according to a recognized signal pattern at a later point of time upon the starting signal.

As an additional input unit, a mouse wheel 20 is provided at the surface of the tactile output unit 12. The mouse wheel 20 is integrated into the tactile output unit 12 so that it is accessible from the outside. It represents a user interface to adjust a characteristic of the sequence of tactile output signals. For example, the user can choose and/or adjust a respiration frequency or amplitude as an input signal for the control unit 16. One further function of the mouse wheel 20 could be to generate a starting signal for initiating the output of tactile output signals when it is pressed by the user. For example, when the user has finished the adjusting procedure, she/he presses the mouse wheel 20 to start the pacing. In the same way he may stop the output of tactile output signals by pressing the mouse wheel 20 another time. A lack of interaction with the user, for example, in a case in which she/he has not performed an input operation for a certain time period can also induce the stopping of the pacing operation.

A mouse wheel 20 is only one possible embodiment of a user interface and can be replaced by a keyboard, one or more buttons or switches, a touch screen, a touch pad, a squeeze sensor, a pressure sensor or the like. Moreover, the user interface can be provided to output status information about the tactile breath pacing device. The status information can be generated by a visual display or an audio signal of any desired type, e.g. indicating lights, a sound signal, or a haptic signal like a buzzer. Moreover, a speaker or a display integrated into or connected to the tactile output unit 12 can be used to output instructions to the user on how to use the device. It is further noted that any input into 14 as described above can also be connected by wire or wirelessly to the tactile output unit 12.

It is noted that the mouse wheel 20 may represent one alternative to the provision of a sensor, that is, a user interface can replace a sensor as an input unit to generate the input signal for the control unit 16. However, it is also possible to combine both functions of a user interface and a sensor in one input unit or to provide different input units, each generating input signals for the control unit 16. Thus a tactile output signal can be generated that is based partially on a user input via the user interface and to another part on a measurement of the respiration behavior of the subject. For example, at least one characteristic of the tactile output signals can be set by the user according to his identity and/or other personal conditions, like his age. This characteristic can be used to set the conditions of the tactile output signals at the start of the pacing process. Measurement results obtained by means of the sensor can be used during the pacing process to adjust and to modify the sequence of tactile output signals. The control unit 16 can also use previously stored parameters, characteristics or algorithms to calculate the tactile output signals.

Figure 2:
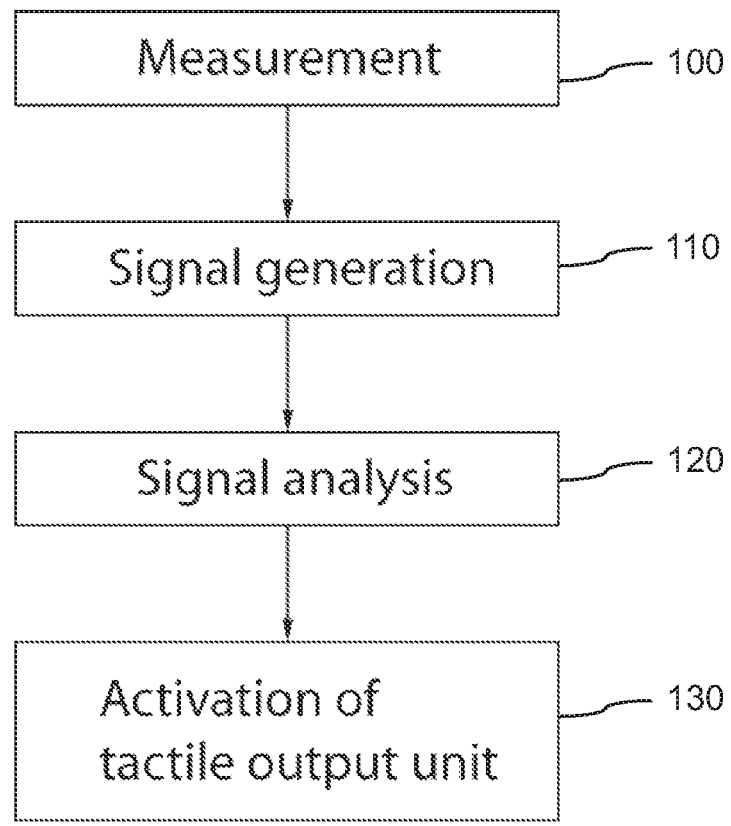
FIG. 2 is a flow diagram showing schematically one embodiment of the inventive method for pacing the respiratory activity of a subject.

The flow diagram in FIG. 2 shows one scenario for a process for generating a pacing signal. In the following description it is supposed that the input signal is generated by the sensor 14 only. The respiration activity of the subject is measured (step 100) by the sensor 14 (as shown in FIG. 1) to generate an input signal indicative of a respiration characteristic of the subject (such as respiration rate) (step 110). This input signal represents the periodic respiration activity including inhale and exhale phases. The input signal is then transmitted to the control unit 16 to be analyzed (step 120). In this analysis, the control unit 16 looks for signal patterns within the input signal. Once a pattern has been recognized, the starting signal is generated for the actuator 18, and the tactile output unit 12 is activated (step 130) to begin with the output of a sequence of tactile output signals. At least at the beginning of this sequence, the tactile output signals comprise a signal pattern corresponding to the recognized signal pattern of the input signal analyzed by the control unit 16 in step 120.

One possibility is to take the inhale to exhale ratio as a reference for generating the tactile output signals. Observations have shown that an inhale to exhale ratio smaller than 1 is beneficial for relaxation. In a case in which a present inhale to exhale ratio of the subject is identified, for example, to be larger than 1 or equal to 1, the tactile output unit 12 may output a sequence of tactile output signals starting with an expand time corresponding to the present inhale time of the subject, which is found to be natural by most persons, but with a contract time larger than the exhale time. Consequently the pacer rate starts with a frequency lower than the measured respiration frequency. It should be noted that a contraction of the tactile output unit 12 may not necessarily be linked to the exhale phase (and consequently, an expansion be linked to the inhale phase), but the roles of the contraction and the expansion can also be reversed.

As already mentioned, the input signal may be generated not by a sensor 14 but can also originate from a user interface as an input unit for adjusting a characteristic of the sequence of tactile output signals. For example, the user adjusts a personal respiration characteristic (frequency, amplitude or the like) by means of the mouse wheel 20, related to her/his identity and personal condition. This can be interpreted as an input signal by the control unit 16 in step 120 in FIG. 2, and according to the result of this analysis, the tactile output unit 12 begins to output of a sequence of tactile output signals.

As an alternative, input signals of the sensor 14 as well as of the user interface, i.e. the mouse wheel 20 can be taken into account. For example, the user may input personal respiration characteristics as described above to determine preconditions for the pacing process. The sensor 14 may then monitor the present respiration activity of the subject, and the control unit 16 will calculate a sequence of tactile output signals on the basis of both kinds of input signals.

To provide guidance for the breathing activity, it is preferred to control the length and frequency of the phases (see FIG. 3) within the sequence of tactile output signals based on the calibration data obtained, so that a relaxing effect takes place. The control unit 16 can determine the further progress of the sequence, beginning with the frequency corresponding to the recognized respiration frequency and changing it in the further course of the tactile output signal.

Figure 3:
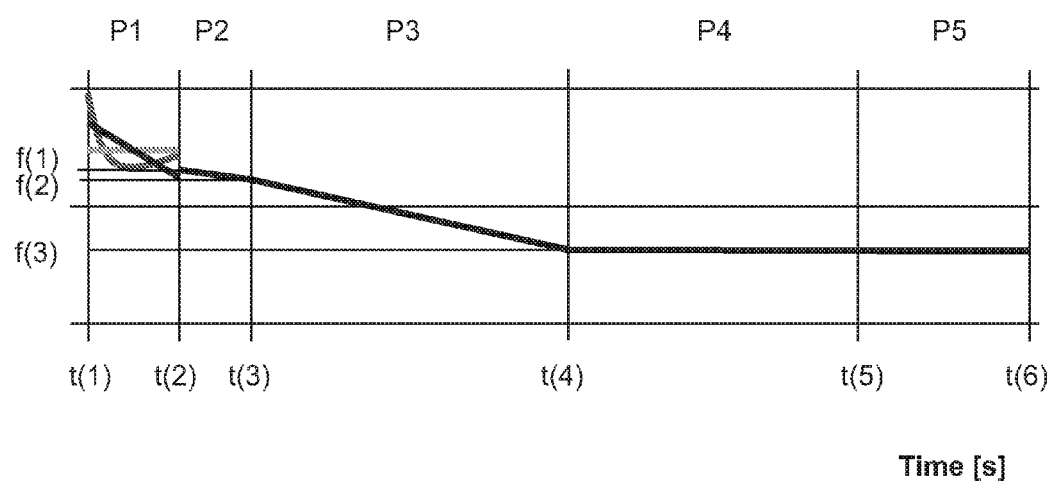
FIGS. 3 and 4 are diagrams demonstrating the development of the pacing rate with time according to one embodiment of the present invention.

The diagram in FIG. 3 shows one possible pacing scenario with respect to the chronological development of the pacing rate (frequency) of the tactile output signal. The horizontal axis of the diagram in FIG. 3 represents the time, while the vertical axis represents the pacing rate. The time axis is divided into five different phases, the first phase beginning at t(1)=0 being a calibration phase (P1), in which the tactile output unit 12 is passive and does not output tactile output signals. The calibration phase (P1) is followed by phases (P2), (P3), (P4) and (P5) in which the tactile output unit 12 is active and outputs a sequence of tactile output signals. This activity period starts with a starting phase (P2) and is followed by a slow down phase (P3), a phase of constant pacing rate (P4) and a fade out phase (P5).

In the calibration phase (P1), the respiration activity of the subject is monitored by the sensor 14 that generates an input signal. This input signal is analyzed by the control unit 16. By this monitoring activity the progress of the respiration of the subject can be analyzed, resulting in a curve that shows characteristics of the respiration activity. In FIG. 3, different curves are shown as three examples of developments of the respiration rate during the calibration phase.

Each curve represents a "respiration rate profile" of the subject. From this profile the control unit 16 can derive a starting point of the pacing activity, that is, a suitable pacing rate at the beginning of the sequence of tactile output signals. The pacing rate (frequency) is only one possible characteristic of the tactile output signal that can be chosen. Another characteristic could be the pacing amplitude that is also derived from the results of the measurements of the calibration phase (P1). Generally speaking, the control unit 16 tries to find a signal pattern within the respiration profile represented by the input signal, and when such a pattern is recognized, a starting signal is generated for the actuator 18 to output a tactile output signal that relates to this signal pattern.

It is also possible to acknowledge results of previous monitoring phases in the search of the signal pattern within the input signal. This means that the calibration phase (P1) shown in FIG. 3 is only one example of such a monitoring phase, in which the tactile output unit is passive. However, such a monitoring phase can also be represented by a previous operation period of the tactile breath pacing device 10 in which the respiration activity of the subject has been monitored. It is also noted that a calibration phase (P1) preceding the output of a sequence of tactile output signals may not always be necessary. The starting point of the pacing activity can rather be chosen merely on the basis of history data, i.e. previous operation periods, as described above.

When the signal pattern has been recognized and the input signal has been generated, the pacing begins at a starting level f(1) of the pacing rate at the time t(2) at the beginning of the starting phase (P2). During this phase (P2) the pacing rate of the tactile output signal slightly decreases in the present embodiment in FIG. 3. The progress of this decrease, i.e. the slope of the curve representing the pacing rate over time can also depend on the calibration results. It is also possible to keep the pacing rate constant during this phase (P2). The starting phase (P2) is followed by a slow down phase (P3) with a stronger decrease of the pacing rate until time t(4). During the slow down phase (P3) the pacing rate decreases from the value f(2) to f(3). This value f(3) corresponds to a target respiration rate of a desired breathing sequence and can be derived from respiratory characteristics measured during the calibration phase. According to one example, the pacing rate f(3) may correspond to a value of 60% or the measured respiration rate at the start.

The slow down phase (P3) is followed by a phase of constant pacing rate (4) in which the pacing rate stays constant on the level f(3). The length of the phase (P4) may be calculated on the basis of previous monitoring periods, i.e. previous operation phases of the tactile breath pacing device 10 and (optionally) the calibration phase (P1). In the slow down phase (P3), the pacing amplitude (not shown) can increase linearly to a certain level and can stay on this level during the phase (P4). Other characteristics of the tactile output signal can also be changed in a predetermined manner during the phases (P2) to (P5).

The phase (P4) is followed by a fade out phase (P5) with a constant pacing rate on the level f(3). In phase (P5), the pacing amplitude may decrease to zero, so that a pacing activity ends at the time t(6) in this example.

While the length of the phases (P4) and (P5) can be determined on the basis of monitoring results, as described above, their length can also be determined on the basis whether there is an input into the sensor 14. When the sensor does not generate an input signal, i.e. the periodic signal indicative of the respiration rate of the subject, this can be taken as a sign that there is no contact between the subject and the tactile output unit 12, and the tactile breath pacing device 10 is not used. It is then possible to start the fade out phase (P5) or the finish the pacing process completely.

The pacing process can be stopped when it has been determined that the subject has fallen asleep or has relaxed to a desired extend. The fade out phase (P5) can be started when a certain characteristic or signal pattern has been recognized within the input signal, or the device is shut down immediately in this case. For example, the sensor 14 may measure a respiration frequency, amplitude or inhale to exhale ratio signalizing a weak breathing activity that indicates a sleeping or deeply relaxed state of the subject. A corresponding signal pattern of the input signal originating from the sensor 14 will be recognized by the control unit 16, and it will generate a stopping signal for the tactile output unit 12 to stop the sequence of tactile output signals immediately or to start the fade out phase (P5) in which the pacing amplitude decreases to zero, and the whole device turns off. In this embodiment the control unit 16 is provided to control the length of the sequence of tactile output signals based on characteristics of the input signal that may correspond to a certain condition of the subject.

What has been described before is only one possible pacing scenario. Another possibility is to dispense the calibration phase (P1) and to derive the respiration rate profile only from previous operation periods of the tactile breath pacing device 10. This means that prior periods of use are taken as monitoring periods in which a signal pattern can be detected.

A third scenario is to acknowledge not only an input signal generated by a sensor 14 but also originating from a user interface like the mouse wheel 20 in FIG. 1. For example, the user may adjust or choose personal respiration characteristics as described above to determine preconditions for the pacing process and input them into the user interface. Such a personal characteristic may refer to the user's identity, the age or another personal feature. This input can then be used as an input signal for choosing a pacing characteristic at the beginning of the sequence of tactile output signals as a "starting point". In the further pacing progress during the phases (P2) to (P5) in FIG. 3, the sequence of tactile output signals can be tuned, i.e. further adapted on the basis of sensor signals that have been collected in a calibration phase or in a phase of prior use as history data.

In all these scenarios it is possible to generate a stopping signal to stop the tactile output unit 12 from further producing tactile output signals. The stopping signal can be generated by the control unit 16 upon the recognition of a certain signal pattern contained within the input signal originating from a sensor 14, as described above. However, other factors can be taken into account, for example, the running time of the sequence so that the stopping signal cannot be generated until a predetermined time period has passed. It is also possible to generate the stopping signal only on a time basis, i.e. to determine a fixed time period as the duration of the sequence or to determine it dependent on a user's input via the user interface. In this embodiment the control unit 16 is provided to control the length of the sequence of tactile output signals based on a time schedule that may be programmed and/or can be changed by the user.

In this version it is possible to influence the output signal by an input unit that can be actively operated by the subject. The user may be enabled to choose between certain preconditions in generating the tactile output signal, for example, to choose between a slower or faster breathing sequence at the beginning of the starting phase (P2). However, there can be the influence of a signal pattern that has been previously recognized so that the generated sequence of tactile output signals can be adapted to the user and is personalized.

Although this is not shown in the present embodiment in FIG. 1, it is possible to provide the tactile breath pacing device 10 with display devices that show the user the operation state of the tactile breath pacing device 10. Such a display device can be a visual display, a light source like a LED or an audio display device giving a sound feedback to the user. This display device can also be arranged externally so that it is not integrated into the tactile output unit 12.

Figure 4:
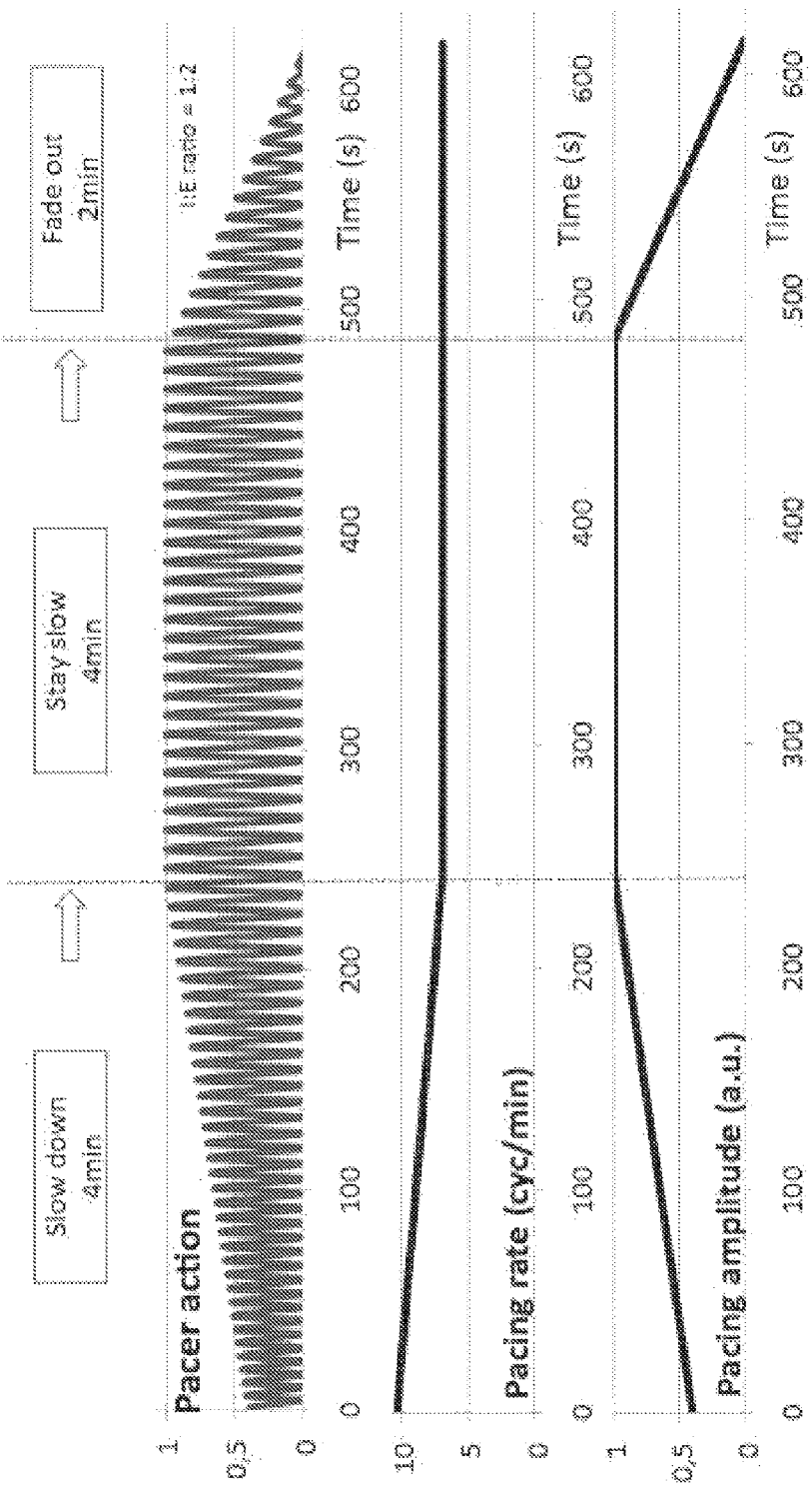

To further explain the change of the characteristics of the tactile output signal in the phases (P3), (P4) and (P5), reference is made to FIG. 4, showing the development of the pacer action over time (horizontal axis) with respect to pacing rate and amplitude. FIG. 4 shows three different curves. The upper curve shows the actual movement (pacer action) of the tactile output unit 12 over time (horizontal axis), the amplitude of this movement extending on the vertical axis. The second curve from above shows the development of the pacing rate (vertical axis) over time, while the third curve shows the development of the pacing amplitude (vertical axis). The amplitude of the pacer action in the upper and the lower curve has been normalized to a value of 1 as a maximum, while the pacing rate is given in pacing cycles per minute.

The development of the pacing rate corresponds to that in FIG. 3, i.e. it decreases in a slow down phase (P3) that lasts for ca. 4 minutes in the present example but stays on a constant level in the following phase (P4) of further 4 minutes and the fade out phase (P5) of 2 minutes. However, the development of the pacing amplitude is different, as it is already indicated in the upper curve. The lower curve shows this development even more clearly: In phase (P3), the amplitude rises linearly towards its maximum, that is reached at the transition from phase (P3) to (P4), stays on a constant level in (P4) and decreases linearly to zero during phase (P5).

FIGS. 5 and 6 show an embodiment of a tactile output unit 12 that is represented by a pad that can be held in a hand 30 of a subject. The control unit 16 and the actuator 18 are integrated into the tactile output unit 12. It is indicated in FIG. 5 that the pad generates haptically perceivable output signals by changing its size, especially its thickness periodically. These output signals can be perceived by a subject when she/he lays its hand 30 onto the output unit 12, as shown in FIG. 5, or by holding the output unit 12 in her/his hand, as indicated in FIG. 6.

FIG. 7 shows the breath pacing device of FIGS. 5 and 6 on a docking station 32 for charging its power supply, which is also integrated into the output unit 12. The docking station 32 can be provided to charge the rechargeable power supply wirelessly based on inductive charging, or both the docking station 32 and the output unit 12 can be provided with suitable electric connectors (like, for example, a plug and a socket) for establishing an electric connection. The docking station 32 can also have other functions, like receiving a user input via a user interface 34 represented by buttons arranged on the top of the docking station 32. The docking station 32 can also comprise sensors as input units for generating the input signal, for example, for detecting the body motion of the subject wirelessly. Moreover, the docking station 32 can optionally be provided with a display, light indicators, a speaker or the like to provide the user with status information. Another option is to provide the docking station 32 with a clock function, preferably as an alarm clock. In this embodiment the docking station 32 would be equipped with a time display, adjusting buttons, an alarm device, etc. A cable 34 is provided for connecting the docking station 32 with a main supply.

Figure 8:
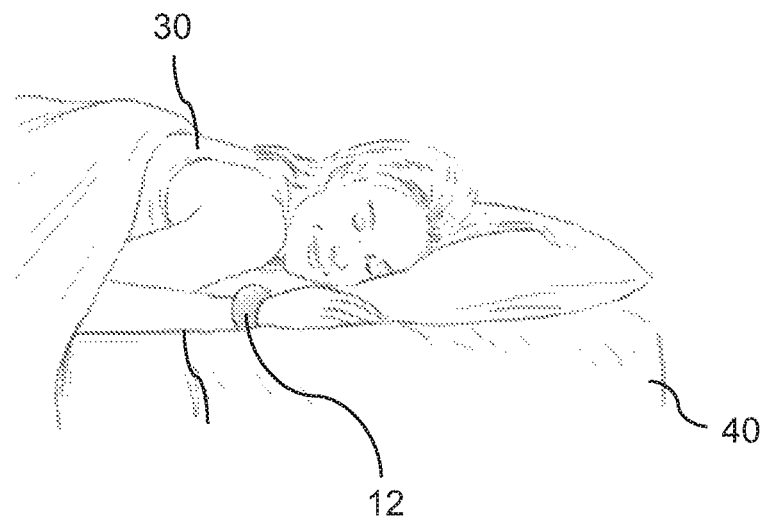
FIG. 8 shows another embodiment of the breath pacing device according to the present invention in use.

FIG. 8 shows another embodiment of an output unit 12 in form of a wristband that is worn by a subject 38 lying on a bed 40. The wristband is provided as a tactile output unit for outputting tactile output signals. For example, the wristband can change its size, and this change can be perceived as an output signal.

Figure 9:
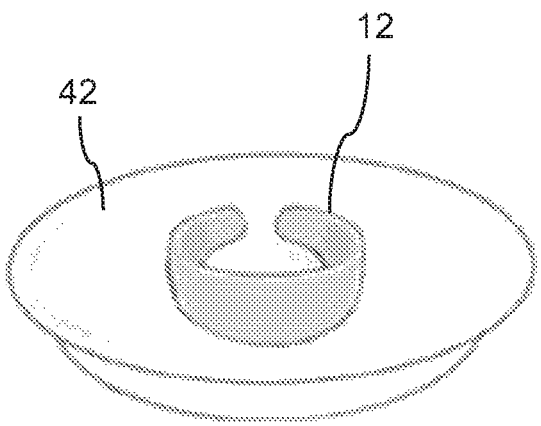
FIG. 9 is a detailed view of the embodiment of the breath pacing device of FIG. 8.

FIG. 9 shows the tactile output unit 12 of FIG. 8 on a plate-like support 42 that may have the same or similar functions as the docking station 32 in FIG. 7. For example, the support 42 may be provided with a recharging function for recharging a rechargeable power supply within the wristband and forms the tactile output unit 12. Other operational units like sensors or a user interface are not shown in FIG. 9. However, the support 42 can also be provided with such features.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A breath pacing device for pacing a respiratory activity of a subject, the breath pacing device comprising:
   an output unit having a continuous surface without holes or apertures when assembled, the output unit configured to:

output a tactile sequence, the sequence having a length comprising a plurality of phases;
an input unit, included within the continuous surface of the output unit, configured to:
generate an input signal related to a measured respiration characteristic of a subject; and
a control unit configured to:
receive the input signal;
initiate a start signal based on one of: a determination of a respiration rate pattern associated with the input signal and a user input,
output the tactile sequence in response to the start signal; and
control the outputted tactile sequence wherein a rate of the outputted tactile sequence is gradually reduced to a predetermined value related to the determined pattern associated with the input signal and an amplitude of the outputted tactile sequence is gradually reduced from a predetermined time after the rate of the outputted tactile sequence achieves the predetermined value, said gradual reduction of amplitude preventing said outputted tactile sequence from being perceivable by the subject.

2. The breath pacing device according to claim 1, wherein the input unit is arranged at the continuous surface of the output unit.

3. The breath pacing device according to claim 1, wherein the input unit is configured to:
receive at least one of:
said characteristic of the subject, said characteristic being provided by one of: a sensor configured to sense the characteristic of the subject; and
a user interface configured to receive said user input.

4. The breath pacing device according to claim 3, wherein said sensor is at least one of: a body motion sensor, a radar sensor, an accelerometer, a camera, a pressure sensor, a photoplethysmographic (PPG) sensor, an airflow sensor, and a weight sensor.

5. The breath pacing device according to claim 4, wherein said pressure sensor comprises a pressure sensitive foil.

6. The breath pacing device according to claim 4, wherein said airflow sensor comprises one of: a temperature sensing element and a microphone.

7. The breath pacing device according to claim 3, wherein the user interface is at least one of: a mouse wheel, a keyboard, at least one button, a touch screen, a touch pad, a squeeze sensor, a pressure switch and a microphone.

8. The breath pacing device according to claim 3, wherein the user interface is configured to:
perform one of: receive the user input to determine the characteristic of a subject, receive the user input to start or stop the outputted tactile sequence and output status information of the breath pacing device.

9. The breath pacing device according to claim 1, wherein the input unit is configured to:
generate the input signal related to at least one of: a respiration frequency, a respiration amplitude, an age and an identification of the subject.

10. The breath pacing device according to claim 1, wherein the control unit is configured to:
control the output of the outputted tactile sequence at least based on an input signal received from one of a sensor and a user interface, wherein the control is further based on one of: a previously stored characteristics and a previously stored algorithm.

11. The breath pacing device according to claim 1, wherein the control unit is configured to:
generate a stopping signal upon receiving an input signal related to a sleeping or relaxed state of the subject after a predetermined time period has lapsed.

12. The breath pacing device according to claim 1, wherein the output unit is at least one of: a cushion, a pillow, a pad, a stuffed toy, a wristband, a mobile phone, and a watch.

13. The breath pacing device according to claim 1, further comprising:
at least one of: a rechargeable power supply and a temperature controlling element.

14. The breath pacing device according to claim 1, wherein a subsequent phase comprises at least one of: a slow-down pacing phase, a constant pacing phase and a fade-out phase.

15. The breath pacing device according to claim 14, wherein the amplitude of the outputted tactile signal is reduced to zero during the fade-out phase.

16. The breath pacing device according to claim 14, wherein a pacing rate associated with the slow-down pacing phase comprises reducing the pacing rate from a first level to a lower second level and a pacing rate of the constant pacing phase and the fade-out phase remains at the second level.

* * * * *